(12) United States Patent
Hampton et al.

(10) Patent No.: US 6,899,686 B2
(45) Date of Patent: May 31, 2005

(54) METHOD AND APPARATUS FOR MONITORING LOCOMOTION KINEMATICS IN AMBULATING ANIMALS

(75) Inventors: Thomas G. Hampton, Framingham, MA (US); José Manuel Otero, Limerick, PA (US); Stephanie Praster, Pensacola, FL (US)

(73) Assignee: The CuraVita Corporation, Boston, MA (US)

( * ) Notice: Subject to any disclaimer, the term of this patent is extended or adjusted under 35 U.S.C. 154(b) by 0 days.

(21) Appl. No.: 10/245,480

(22) Filed: Sep. 17, 2002

(65) Prior Publication Data

US 2003/0055362 A1 Mar. 20, 2003

Related U.S. Application Data

(60) Provisional application No. 60/322,563, filed on Sep. 17, 2001.

(51) Int. Cl.$^7$ ............................ A61B 5/103; A61B 5/117

(52) U.S. Cl. ........................................ 600/595; 119/700

(58) Field of Search ................................. 600/595, 587; 119/700, 701, 712

(56) References Cited

U.S. PATENT DOCUMENTS

| | | | | |
|---|---|---|---|---|
| 3,485,213 A | * | 12/1969 | Scanlon ...................... | 119/700 |
| 4,600,016 A | * | 7/1986 | Boyd et al. ................. | 600/595 |
| 4,631,676 A | * | 12/1986 | Pugh .......................... | 600/595 |
| 5,299,454 A | * | 4/1994 | Fuglewicz et al. ........... | 73/172 |
| 6,010,465 A | * | 1/2000 | Nashner ...................... | 600/595 |
| 6,231,527 B1 | * | 5/2001 | Sol ............................. | 600/595 |

OTHER PUBLICATIONS

Kram, R., Wong, B. and Full, R.J. 1997. "Three–Dimensional Kinematics and Limb Kinetic Energy of Running Cockroaches". The Journal of Experimental Biology 200, 1919–1929.*

Birch et al. 2001. "A miniature Hybrid Robot Propelled by Legs". Proceedings of the 2001 IEE/RSJ International Conference on Intelligent Robots and Systems, P 845–851.*

Macmillan, D.L. "A Physiological Analysis of Walking in the American Lobster". Feb. 6, 1975. Biological Sciences (England) vol. 270.*

(Continued)

Primary Examiner—Max F. Hindenburg
Assistant Examiner—Jonathan Foreman
(74) Attorney, Agent, or Firm—Lahive & Cockfield, LLP

(57) ABSTRACT

A method and apparatus for recording and analyzing the gait of an animal is provided. The apparatus can take the form of a gait imaging system. The system includes a movable belt track upon which a subject can ambulate. An imaging device is disposed below the belt track to record contact between at least one limb of the subject and the belt track. The subject can ambulate along the belt track in a substantially stationary location above the imaging device as the belt track moves, and the imaging device can record the contact by the subject. A method of recording a gait of an ambulating subject is also provided. The method includes locating the subject on a movable belt track. The subject is motivated to ambulate along the movable belt track at about the same rate as the movable belt track, while the belt track is moving, such that the location of the subject does not substantially change. Contact made by at least one limb of the subject with the belt track is recorded with a recording device underneath the belt track. Additional kinematic analysis can occur of the subject's gait. The method of recording can further include transmission of the gait images to a computing apparatus. The computing apparatus can identify footprint image data, including filtering out unwanted noise. The computing apparatus can then carry out the kinematic analysis, including calculation of physiological information relating to the subject.

25 Claims, 8 Drawing Sheets

OTHER PUBLICATIONS

Allen, William H. "Animals and their Models do their Locomotions: Biologists Probe Mechanics and Energetics of Animal Motion". Jun. 1995. Biosciences. vol. 45, No. 6, pp. 381–383.*

Clarke, K.A. and J. Still "Gait Analysis in the Mouse" *Physiology & Behavior* 66(5):723–729 (1999).

Clarke, K.A. and J. Still "Development and consistency of gait in the mouse" *Physiology & Behavior* 73:159–164 (2001).

Gurney, Mark E. et al. "Motor Neuron Degeneration in Mice That Express a Human Cu,Zn Superoxide Dismutase Mutation" *Science* 264:1772–1775 (Jun. 17, 1994).

* cited by examiner

METHOD AND APPARATUS FOR MONITORING LOCOMOTION KINEMATICS IN AMBULATING ANIMALS

RELATED APPLICATION

This application claims priority to co-pending U.S. Provisional Application No. 60/322,563, filed Sep. 17, 2001, for all subject matter common to both applications. The disclosure of said provisional application is hereby incorporated by reference in its entirety.

FIELD OF THE INVENTION

The present invention relates to an apparatus and method suitable for monitoring locomotion kinematics in ambulating animals, and more particularly to monitoring, measuring, and imaging the gait of a small animal, such as a mouse.

BACKGROUND OF THE INVENTION

Animals, for example mice, are used extensively in the examination of gene function, the development of drugs, and in other laboratory research applications. Often, the animals are constantly moving around, making it difficult to examine them for measurements of physiological parameters. However, mice are desirable mammalian models for examining locomotion kinematics, such as stride length, foot placement, and speed of ambulation.

A conventional method for measuring locomotion indices, such as stride, is by painting the feet of the mice and allowing the mice to walk on a clean, stationary, sheet of white paper. Analysis of the tracks created by the painted feet of the mice can be interpreted for derivation of the gait and stride indices. See for example, Gurny, M E et al., *Science* 264:1772–1775, 1994.

Another conventional method for measuring locomotion indices is described in Clarke and Still, *Physiology and Behavior* 66:723–729, 1999. The method involves gait analysis in a mouse using simultaneous video and reaction force analysis. An extension of a similar system described by Clarke for rats can be found in Physiological Behavior 58:415–419, 1995. The system for rats consisted of two cameras positioned below a U-shaped Plexiglas tunnel about 12 inches in length. One or two cameras positioned below the central part of the tunnel record under-views of the walking mouse. The images of the walking mouse are recorded on videotape. The videotape is then analyzed for locomotive indices. A minimum number of steps, about six, is needed for robust interpretation of the data. A longer tunnel would better provide the space required to obtain good data of the walking mouse. However, a longer tunnel would require additional cameras, movement of the camera approximately at the same speed as the walking mouse, or rotation of the cameras following an approaching mouse and a departing mouse. The last option results in some optical distortion as the viewing angle of the mouse changes, along with the distance to the mouse.

SUMMARY OF THE INVENTION

There is a need in the art for a system and method for recording and analyzing the gait of an animal that simplifies the acquisition of data and images, improves the quality of data and images retrieved, and increases the amount of data obtainable without significantly increasing the time or complexity of the data acquisition process. The present invention is directed toward further solutions to address this need.

A gait imaging system is provided. The system includes a movable belt track upon which a subject can ambulate. An imaging device is disposed below the belt track to record contact between at least one limb of the subject and the belt track. The subject can ambulate along the belt track in a substantially stationary location above the imaging device as the belt track moves, and the imaging device can record the contact by the subject.

In accordance with aspects of the present invention, the belt track can be a substantially transparent belt track through which the imaging device can view the contact of the subject with the belt track. The imaging device can take the form of a camera, camcorder, or a digital image capturing device, suitable for recording ambulation of the subject over a desired period of time.

In accordance with further aspects of the present invention, the belt track can be a belt having a markable surface. The imaging device can be a reservoir of ink upon which the at least one limb of the subject can apply pressure, through the belt track, transferring ink from the reservoir to the markable surface of the belt track.

In accordance with further aspects of the present invention, the speed of movement of the belt track is adjustable. The system can further include a structure disposed to substantially surround the subject while the subject is on the belt track, for motivating the subject to ambulate when the belt track is moving and prevent the subject from escape. The structure can have a plurality of walls forming an enclosure hovering above the moving belt track. The structure can have one or more additional enclosures for motivating more than one subject to ambulate concomitantly.

In accordance with further aspects of the present invention, the system can further include a computing apparatus supporting a software application for manipulating and analyzing the data from the recorded subject contact. The software application can identify placement of the at least one limb of the subject based on the recorded subject contact. The software application can execute at least one algorithm for analysis of a gait of the subject based at least in part on the subject contact. The imaging device can record images at a rate of at least about 60 frames per second.

In accordance with another aspect of the present invention, a method of recording a gait of an ambulating subject is provided. The method includes locating the subject on a movable belt track. The subject is motivated to ambulate along the movable belt track at about the same rate as the movable belt track, while the belt track is moving, such that the location of the subject does not substantially change. Contact made by at least one limb of the subject with the belt track is recorded with a recording device underneath the belt track.

In accordance with further aspects of the present invention, locating includes placing the subject within an enclosure hovering above the movable belt track. Motivating the subject includes initiating movement of the belt track while the subject is surrounded by an enclosure, such that the subject must ambulate to avoid collision with the enclosure. Recording includes utilizing at least one of a camcorder and a digital image capturing device to record contact made by the at least one limb of the subject with the belt track for a desired period of time. The belt track can be sufficiently transparent to enable viewing of the contact made by the at least one limb from underneath the belt track.

In accordance with further aspects of the present invention, recording includes transferring ink from an ink reservoir underneath the belt track to a markable surface of the belt track upon each instance of the at least one limb of the subject applying pressure, through the belt track, to the ink reservoir.

In accordance with further aspects of the present invention, the method further includes forwarding information relating to the contact made by the at least one limb to a computing apparatus supporting a software application for analyzing the gait of the subject based on the recorded contact. The method further includes reading the information to a data storage device. The method further includes converting the information to a standardized format. Recording can occur at a rate of at least about 60 frames per second. The method can further include identifying footprint image data from the contact made by at least one limb of the subject with the belt track. Extracting can include converting image data to binary and filtering out noise, leaving footprint image data. The method can also include calculating physiological information based on the footprint image data.

BRIEF DESCRIPTION OF THE DRAWINGS

The present invention will become better understood with reference to the following description and accompanying drawings, wherein.

DETAILED DESCRIPTION

Figure 1:
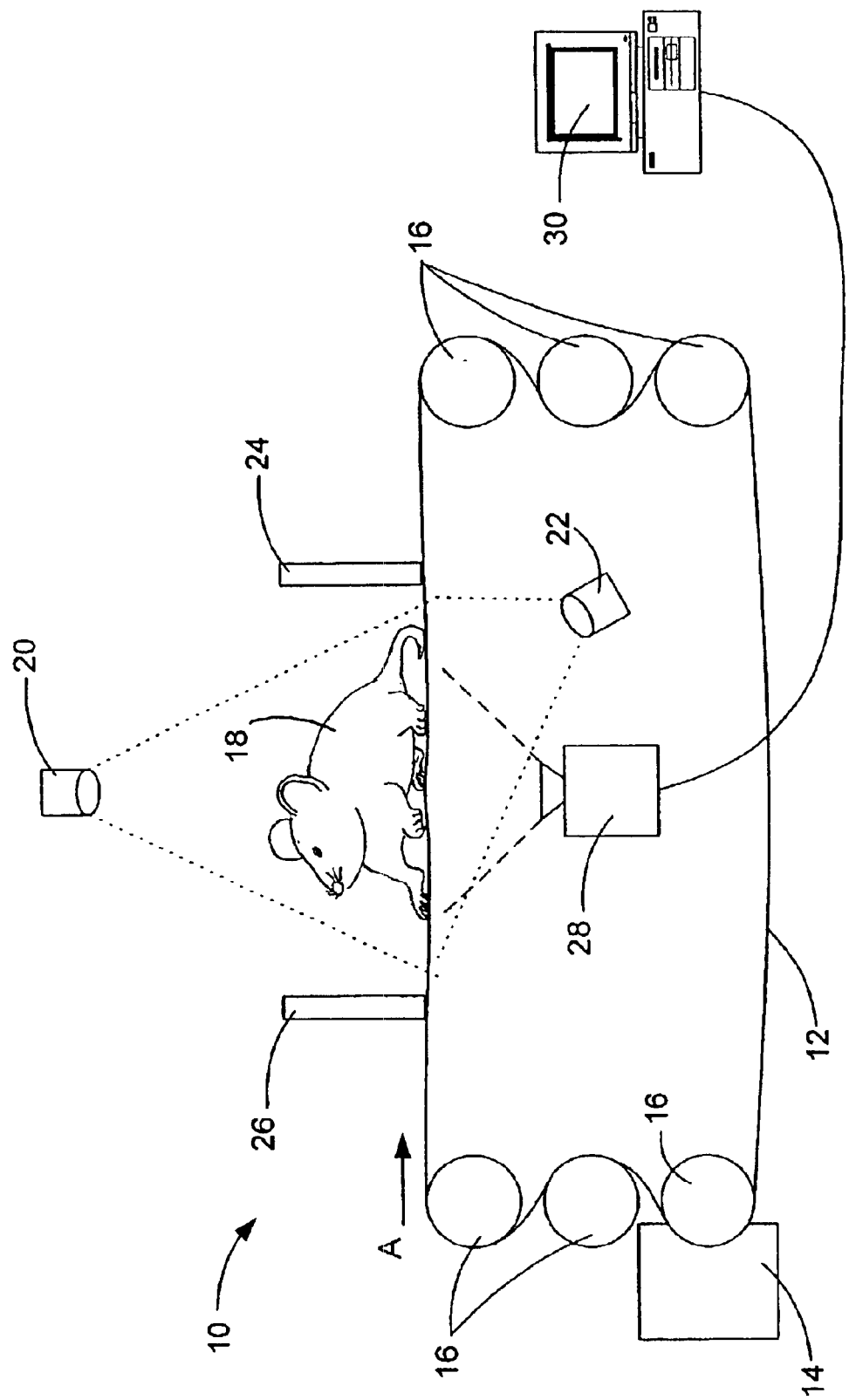
FIG. 1 is a diagrammatic illustration of a locomotion monitoring apparatus, according to one aspect of the present invention.

An illustrative embodiment of the present invention relates to a locomotion monitoring apparatus for capturing the image of relatively large quantities of steps taken by animals, such as mice. The apparatus includes a motor-driven belt upon which the mouse is positioned. The belt can be substantially transparent or translucent. The motor drives the belt, and a partition, or other mechanism, motivates the mouse to ambulate to maintain approximately the same lateral position. An image capturing device captures and records the dynamic motion of the limbs of the mouse, and in particular the footprints, as the mouse ambulates on the belt. Because the belt is motor driven, the number of steps taken by the mouse and recorded by the monitoring apparatus is limited only by time spent on the belt and ability of the mouse to continue ambulating. For purposes of illustration, the small animal will be described and illustrated as a mouse. However, one of ordinary skill can appreciate that other animals can be monitored using the apparatus of the present invention. Further, the size of the animal monitored and the size of the apparatus can be scaled up or down, accordingly.

FIGS. 1 through 6, wherein like parts are designated by like reference numerals throughout, illustrate example embodiments of an apparatus for monitoring locomotion kinematics in ambulating animals, according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 shows an example embodiment of a locomotion monitoring apparatus 10. The apparatus 10 includes a belt 12 that weaves between a plurality of rotating drums, cogs, or wheels 16. The wheels 16 enable the belt 12 to move in a circumnavigating motion. The belt 12 is substantially transparent or translucent. A motor 14 couples to at least one of the wheels 16, forming a driving wheel for providing the motion to the belt 12. At least one mouse 18 can ambulate along the belt 12 as described herein.

A number of different materials can be used to form the belt 12. The resulting belt 12 must be pliable enough, and strong enough, to be repeatedly flexed as it travels through the wheels 16 while in motion. In addition, the belt 12 must be sufficiently transparent to permit a camera, or other image collection device, to see through the belt 12 from underneath to observe the ambulating animal, in accordance with one embodiment of the invention and as further discussed herein. Alternatively, the belt 12 must be sufficiently transparent to heat emissions, such that a heat sensing camera can see through the belt 12 to observe the ambulating animal.

The motor 14 can be an electric motor. The motor 14 can further have a single speed, multiple speeds, or be infinitely variable. The different speeds made available by the motor 14 results in the motor 14 being able to move the belt 12 at different rates and urge the mouse to ambulate at different rates.

An image collection device 28, in accordance with one embodiment, is disposed beneath the belt 12. The image collection device 28 can take the form of, for example, a camera, a video camera, a digital camera, a digital camcorder, a digital image capture device, and the like. The image collection device 28 can also take the form of an ink pad, touch pad, or other pressure sensing pad or technology, as will be discuss in a later embodiment herein.

The image collection device 28 can capture the image of the mouse 18 ambulating along the moving belt 12 above. At least one light can aid in the capturing of the image. For example, a first light 20 can shine from above the mouse 18 to provide better contrast between the mouse 18 and the background. A second light 22 can shine from beneath the belt 12, to highlight the feet of the mouse 18 as they make contact with the belt 12. The position and use of the lights 20 and 22 can vary as situations dictate, and as understood by one of ordinary skill in the art.

The mouse 18 is motivated to move as the belt 12 moves because a back partition 24 prevents the mousel 8 from being able to ride the belt 12 backwards. As the belt 12 moves the mouse 18 backwards, the mouse 18 eventually makes contact with the back partition 24, which urges the mouse 18 to begin ambulating. A front partition 26 can be disposed in front of the mouse 18 to prevent the mouse 18 from running faster than the belt 12, and running off of the front. In addition, the image collection device 28 can maximize the magnification of the image if the image collection device 28 is given a more limited span to view. By including the front partition 26, this limits the mouse 18 to ambulate in the more limited span of between the back partition 24 and the front partition 26.

Figure 2A:
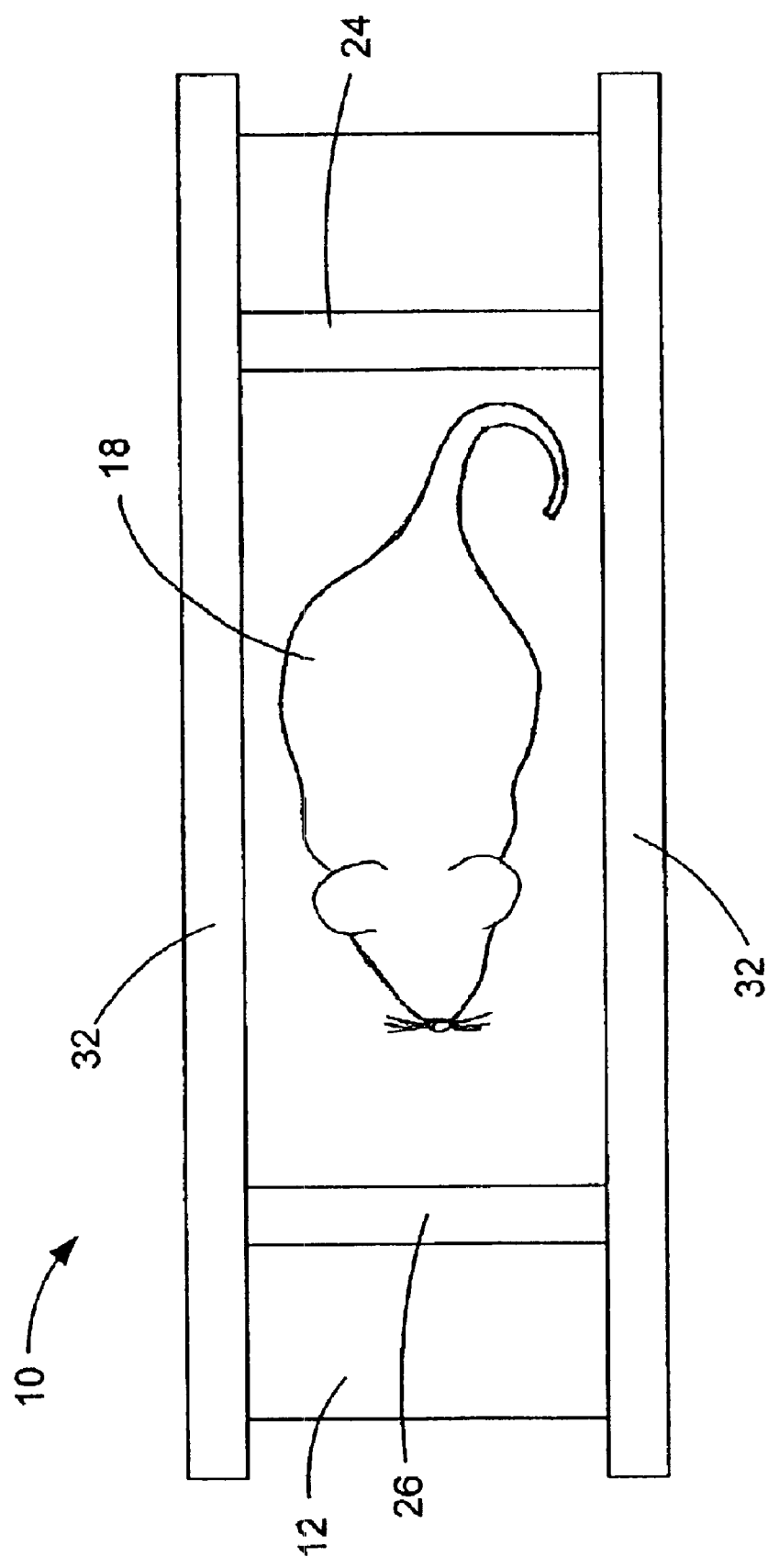
FIG. 2A is a top view of a portion of the apparatus of FIG. 1, according to one aspect of the present invention.
Figure 2B:
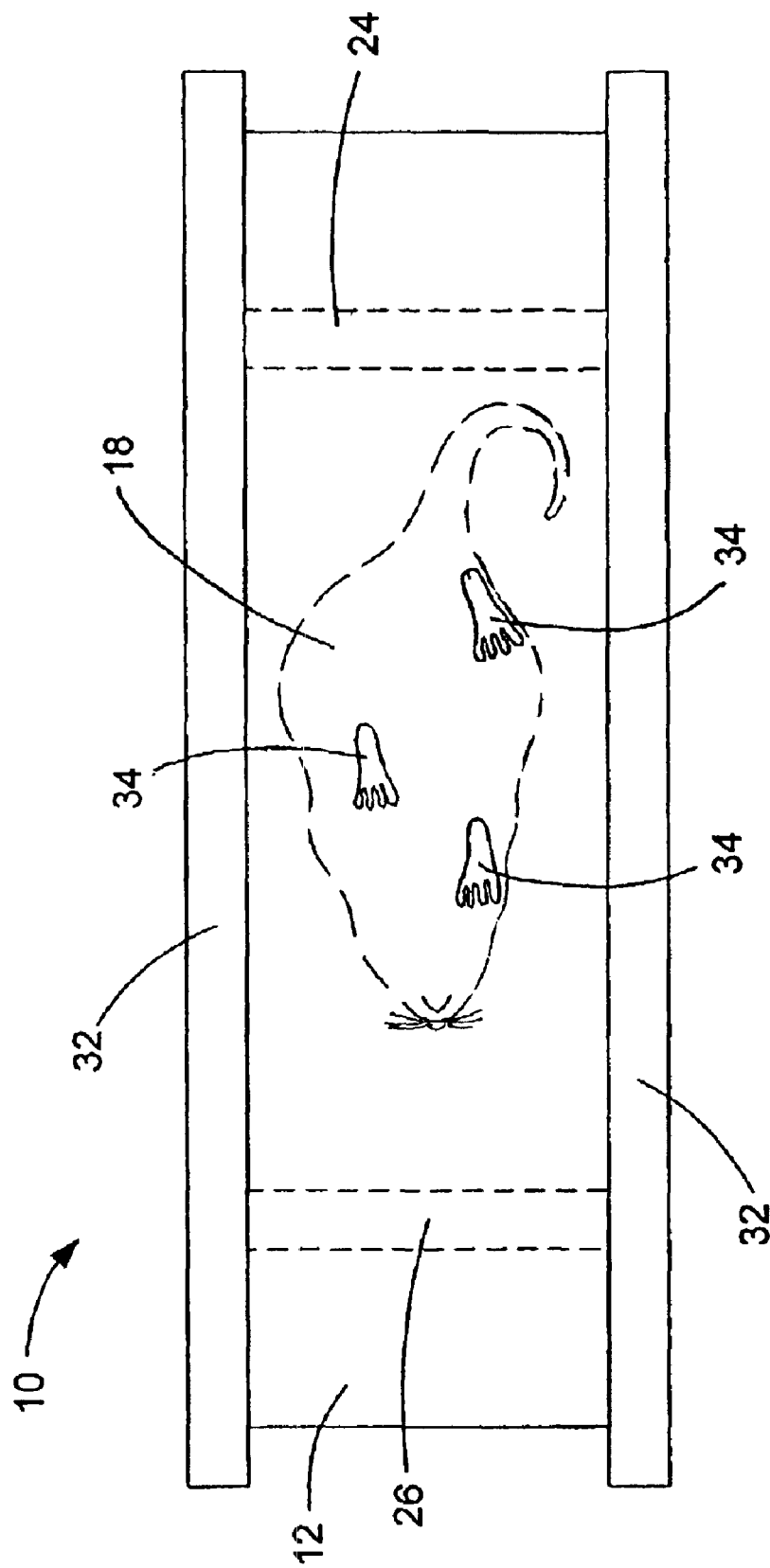
FIG. 2B is a bottom view of a portion of the apparatus of FIG. 1, according to one aspect of the present invention.

FIGS. 2A and 2B additionally show side walls 32 on either side of the mouse 18. The side walls are not required, but can be helpful in preventing the mouse 18 from ambulating off the side of the belt 12 as the belt 12 is in motion.

A computing apparatus 30 can communicate with the image collection device 28 and/or the motor 14. Computing apparatus 30, as used herein, refers to a programmable device that responds to a specific set of instructions in a well-defined manner and can execute a set of instructions. The computing apparatus can include one or more of a storage device, which enables the computing apparatus to store, at least temporarily, data, information, and programs (e.g., RAM or ROM); a mass storage device for substantially permanently storing data, information, and programs (e.g., disk drive or tape drive); an input device through which data and instructions enter the computing apparatus (e.g., keyboard, mouse, or stylus); an output device to display or produce results of computing actions (e.g., display screen, printer, or infrared, serial, or digital port); and a central processing unit including a processor for executing the specific set of instructions.

A connection between the computing apparatus 30 and the image collection device 28 enables a user of the apparatus 10 to control the image collection device 28 in its acquisition of images of the ambulating mouse 18. In addition, the connection enables the image collection device (for example, if it is a digital camera or digital camcorder) to transmit images of the ambulating mouse 18 to the computing apparatus 30 for analysis, as described later herein.

FIGS. 2A and 2B illustrate a portion of the locomotion monitoring apparatus 10 from views above and below the apparatus 10, respectively. As the belt 12 moves, the mouse 18 ambulates, surrounded on all four sides by the back partition 24, front partition 26, and side walls 32. Again, the side walls 32 and front partition 24 are not requirements of the invention, they can however, aid in motivation of the mouse 18 to ambulate. As the mouse 18 ambulates, the feet or paws of the mouse 18 make contact with the belt 12, which results in images of the underside of all or part of the feet in the form of footprints 34. In the case of the relatively transparent belt 12, the contact of the feet or paws with the belt 12 improves the view of the feet or paws relative to the other portions of the mouse 18. FIG. 2B illustrates the view of the footprints 34 that result from the contact of the feet or paws with the belt 12. Analysis of the footprints 34 can be performed, either manually or using the computing apparatus 30 and associated software, to analyze the locomotion kinematics of the mouse 18, including gait.

Figure 3:
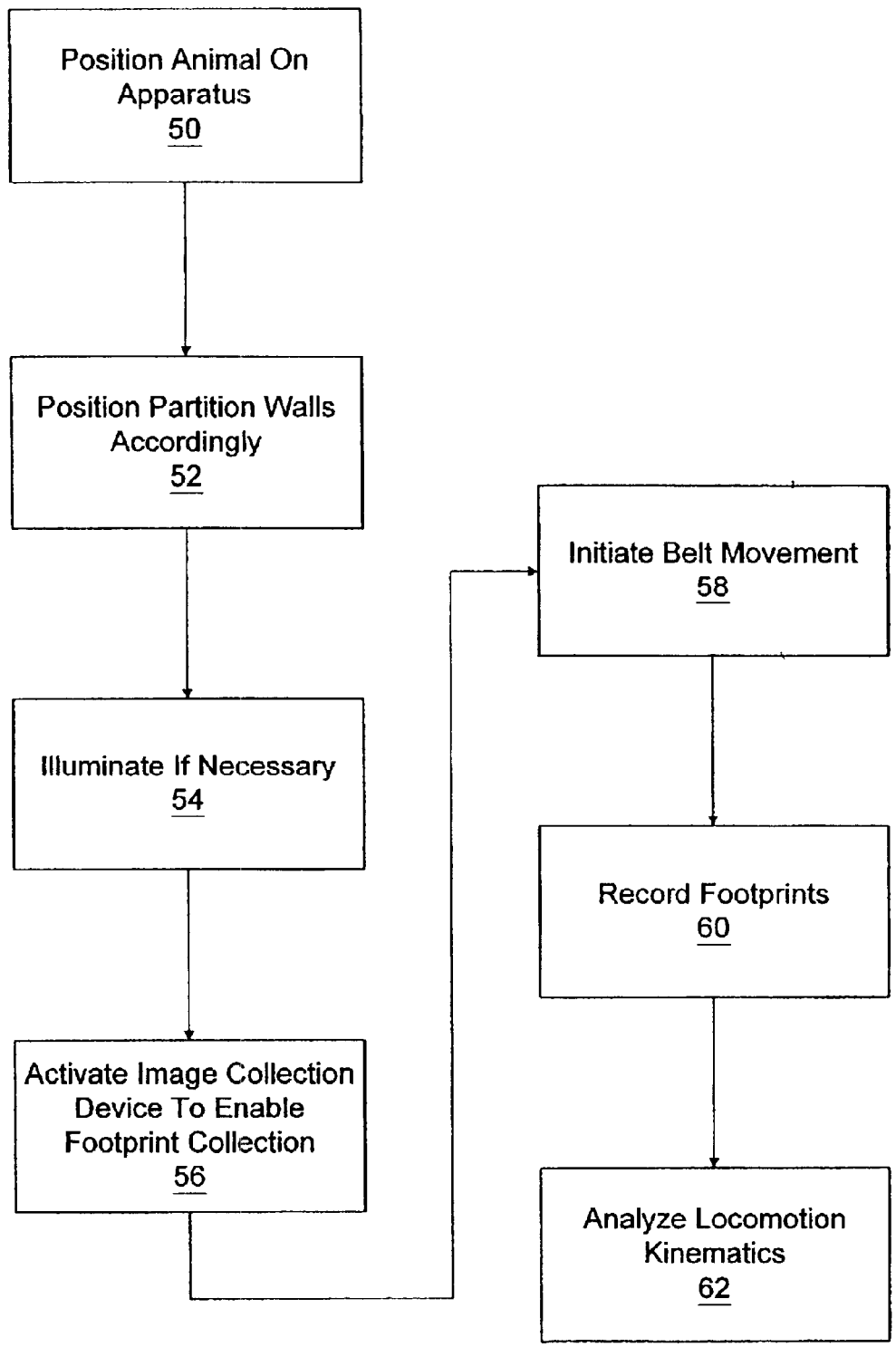
FIG. 3 is a flow chart illustrating a method of monitoring, according to one aspect of the present invention.

In operation as shown in FIG. 3, the teachings of the present invention enable the monitoring, measuring, and imaging of the gait and general locomotion kinematics of a small animal, such as a mouse. In accordance with one example embodiment, if not already on the belt 12, the mouse 18 is placed on the belt 12 of the locomotion monitoring apparatus 10 (step 50). Each of the rear partition 24, front partition 26, and side walls 32, if not already in position, can be inserted into position (step 52). For better illumination, an operator can turn on the first light 20 and/or the second light 22 (step 54). However, the lighting step is optional, based on environmental conditions. In addition, continual adjustments of the lighting can be made throughout the monitoring process.

At some point during the process, the image collection device 28 must be activated to gather the footprints 34 of the mouse 18 (step 56). The operator initiates the belt 12 operation, causing the belt 12 to begin circumnavigation through the wheels 16 (step 58). One of ordinary skill will appreciate that the belt 12 need not circumnavigate, but could be spooled or stored at one end and fed through the wheels 16 to a destination location, without circumnavigation. In addition one of ordinary skill in the art can appreciate that the wheels 16 are shown to rotate such that the belt moves in the direction of arrow A, but that the direction of movement can be reversed.

As the belt 12 begins to move, the mouse 18 moves toward the back partition 24 until the mouse 18 either beings ambulating or collides with the back partition 24. If the mouse 18 does collide with the back partition 24, there is a substantial motivation for the mouse to begin ambulating to correct the state of collision. Thus, the back partition 24 urges the mouse to ambulate while the belt 12 is moving. The image collection device 28 records the footprints 34 of the mouse 18 as the mouse 18 ambulates (step 60). The image collection device 28 can operate at a number of different recording speeds, however it has been found that using current technology, a rate of at least about 60 frames per second is preferable, and a rate of between about 60 frames per second and about 90 frames per second was found to be adequate. One of ordinary skill will appreciate that the recording rate can be adjusted to accommodate new recording technology, and different analysis processes. At some point after the collection of the footprints 34, analysis occurs to determine the locomotion kinematics accordingly (step 62). The analysis need not take place in conjunction with the recording of the ambulating, nor within any specified amount of time following the recording of the ambulating. However, analysis can occur contemporaneous with, or subsequent to, recording of the ambulating images.

The locomotion monitoring apparatus 10 captures images of mice from underneath as they are urged to ambulate upon, and counter to, the direction of a moving motor driven belt. Discrete images of portions of the feet of the animal as it ambulates, are spliced together, either physically or in digital format. The images generate a dynamic map of the articulation and timing of foot movement of the animal through an unlimited number of continuous strides not bounded by a walking track of finite length. The movement of the belt enables the image collection device 28 to remain stationary, thus avoiding distortion of the footprint image from the image collection device 28 either angling to capture a moving animal, or moving laterally to stay approximately beneath an animal as it ambulates. Thus, the locomotion monitoring apparatus 10 enables the acquisition of gait signals based on sequential steps of an ambulating animal as viewed from a fixed location.

If desired, or if configured appropriately, the image collection device 28 can be operated or controlled by the operator inputting instructions into the computing apparatus 30 to guide the operation of the image collection device 28. In addition, the image collection device 28 can transfer the footprints 34 to the computing apparatus 30 for analysis of the locomotion kinematics by the computing apparatus. Further, the computing apparatus 30 can convey instructions to the image collection device 28 to transmit or store the images accordingly.

Figure 4A:
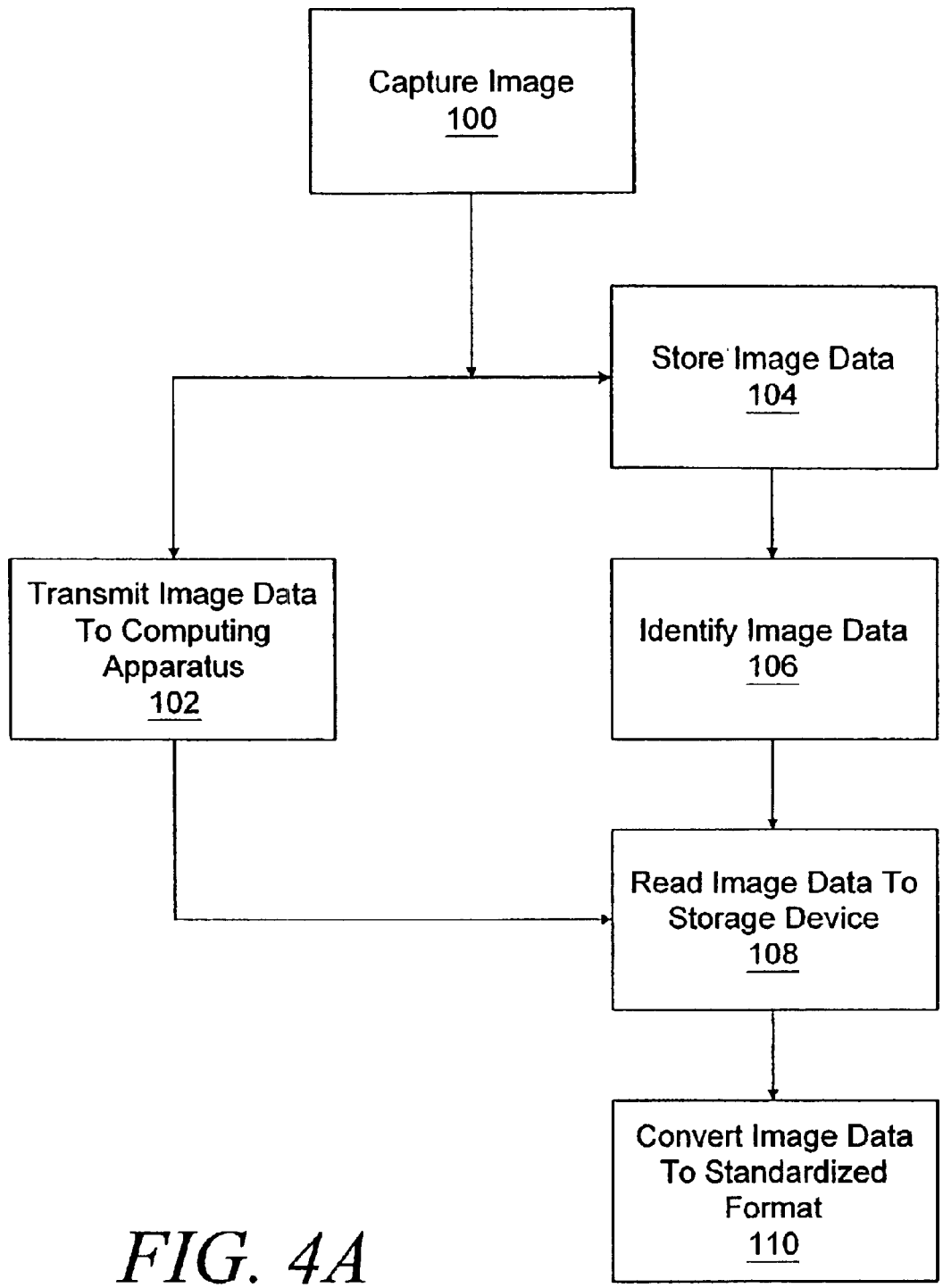
FIG. 4A is a flow chart illustrating a method of image data capture.

The computing apparatus 30 can include one or more software applications that can take gait image information from the image collection device 28 and analyze the image information to determine locomotion kinematics of the ambulating mouse 18. FIG. 4A illustrates the taking of gait image formation, and subsequent data manipulation. The image collection device 28 captures the image of the mouse 18 ambulating on the belt 12 (step 100). The image collection device 28 can either directly transmit the image data to the computing apparatus 30 (step 102) or store the image data on a storage device, such as a video cassette or digital cassette (step 104). If stored on a cassette, the computing apparatus 30 must first identify the image data (step 106), and read the identified image data to a storage device associated with the computing apparatus 30 (step 108). The computing apparatus 30 can then convert the image data to a standardized format, such as AVI format (step 110).

Figure 4B:
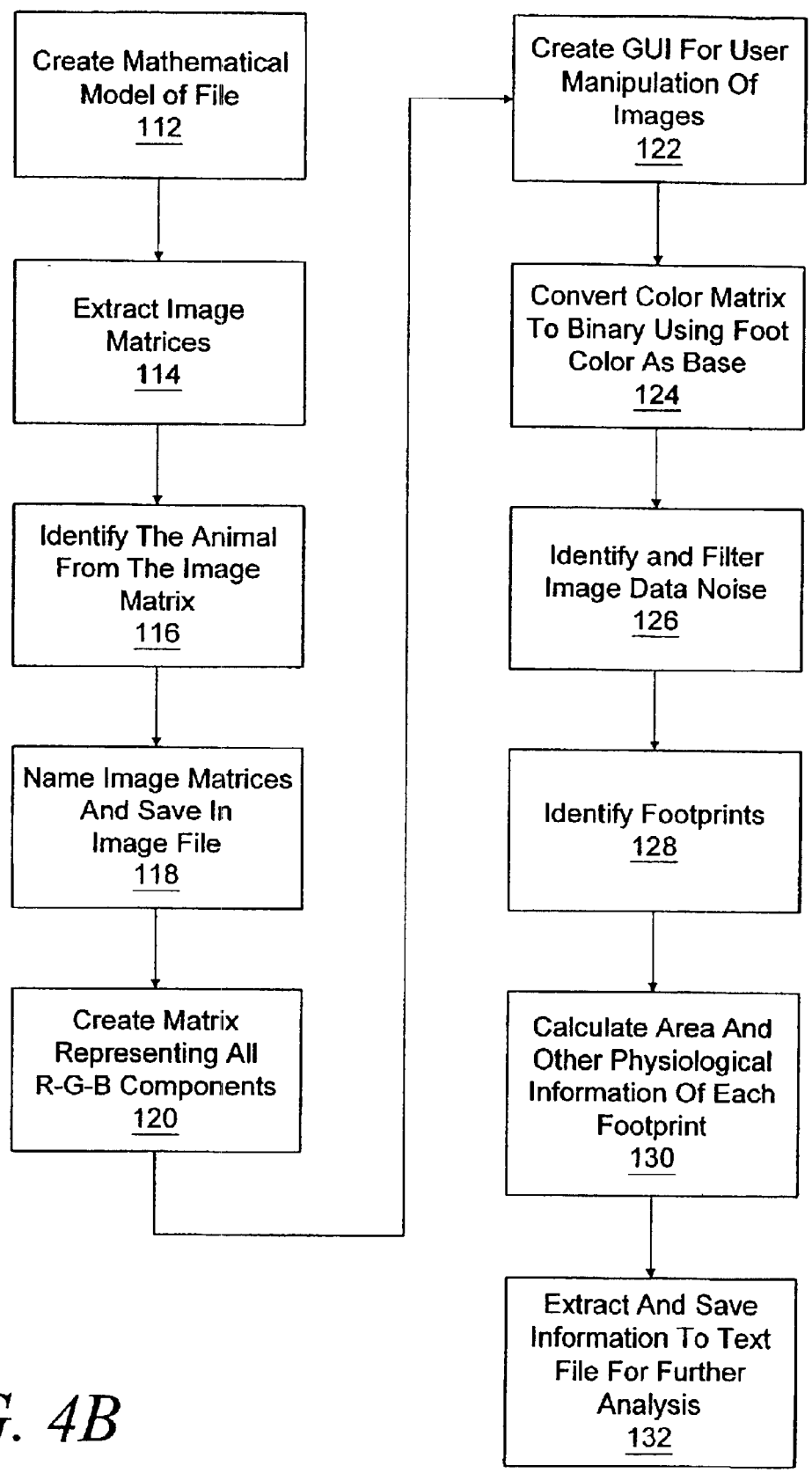
FIG. 4B is a flow chart illustrating a method of image data manipulation and analysis.

FIG. 4B illustrates the extraction of the images from the standardized AVI format to a JPG image. The computing apparatus 30 reads the desired AVI file and creates a Multi Matrix Mathematical Model of the AVI file (step 112). Image matrices are then extracted for each frame associated with the AVI file (step 114). Using a rule-based selection criterion, the mouse is identified from the image matrix (step 116). The computing apparatus 30 then names the image matrix with, for example, a sequential numbering system, and saves the image matrix as a JPG file (step 118).

Once JPG (or other standardized format) files are created, the computing apparatus 30 can continue with the analysis. The computing apparatus 30 sequentially reads images into memory and creates a matrix representing all the red, green, and blue color components of each pixel of the image (step 120). A graphical interface is created for the user to refine a default criterion or to choose a new criterion, if desired, to identify mouse 18 paw color as seen in the image (step 122). The color image matrix is then converted to a binary equivalent, using the paw color as a base (step 124). The image data noise is identified and filtered based on size, shape, and positioning of the identified and probable paw like regions in the image (step 126). The particular paw of the four mouse paws is identified in each instance as left-front, right-front, left-rear, or right-rear, accordingly (step 128). The area of each paw or footprint 34 is then calculated, in addition to other desirable physiological information, such as X and Y coordinates of paw placement, bounding box, orientation, timing, and the like (step 130). The physiological information can be further analyzed to determine locomotion kinematics of the ambulating mouse 18. The extracted information is then saved to a text base format, such as Microsoft Word® or Microsoft Excel® format (Word® and Excel® are produced by the Microsoft Corporation, Redmond, Wash.) for reporting purposes and further user analysis (step 132).

Figure 5:
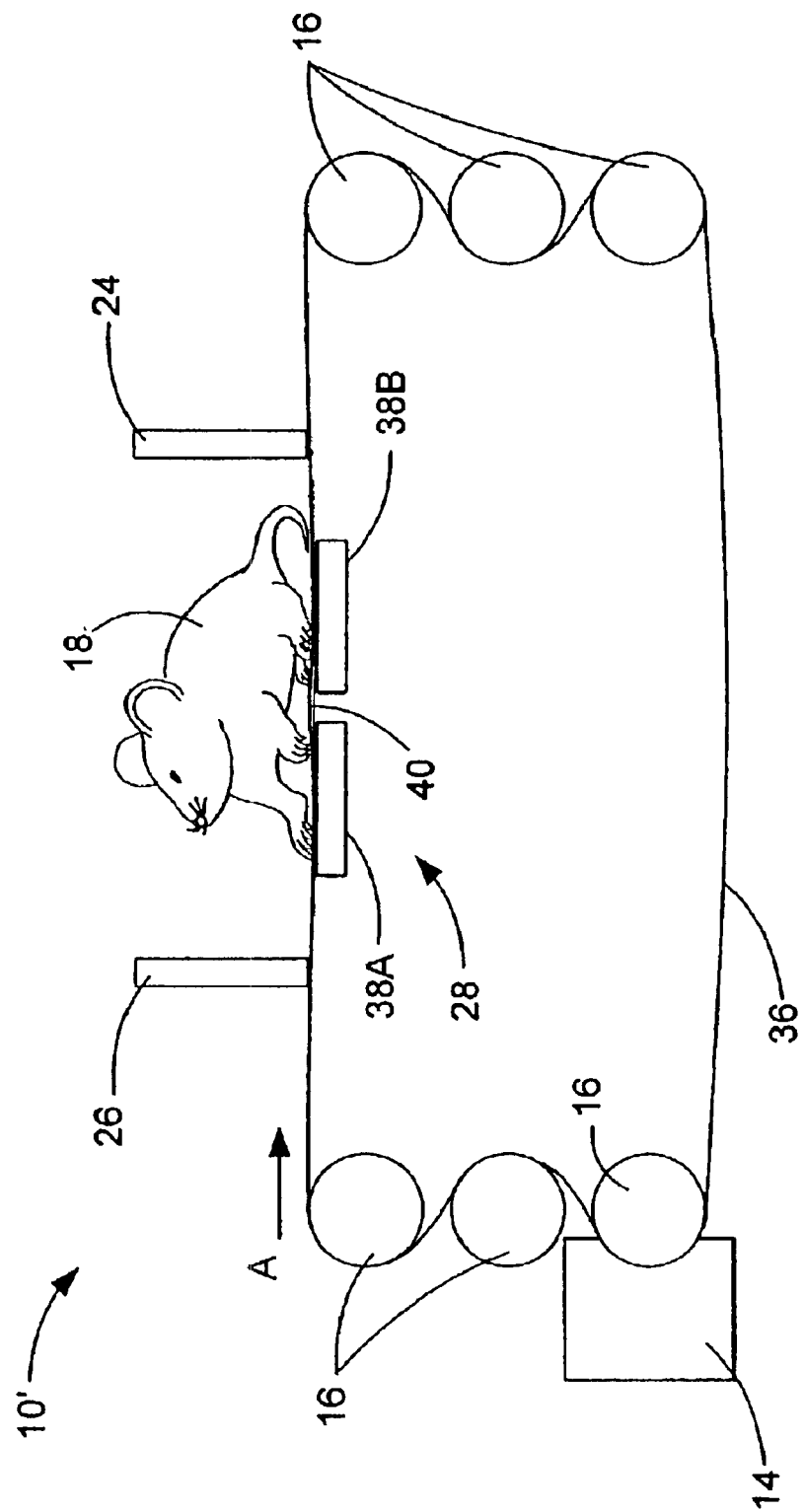
FIG. 5 is a diagrammatic illustration of another embodiment of the locomotion monitoring apparatus, according to one aspect of the present invention.

FIG. 5 illustrates another example embodiment of a locomotion monitoring apparatus 10' in accordance with the teachings of the present invention. The locomotion monitoring apparatus 10' includes a number of same or similar elements as the embodiment depicted in FIG. 1, in addition to some variations. For example, the locomotion monitoring apparatus 10' includes a paper belt 36 that weaves between the plurality of wheels 16. The wheels enable the belt to move in a circumnavigating motion. The motor 14 couples to at least one of the wheels 16, forming a driving wheel for providing the motion to the paper belt 36. At least one mouse 18 can ambulate along the paper belt 36.

In the example embodiment, the paper belt 36 is formed of paper or a paper-like surface that can flex around the wheels 16 and is strong enough not to break, while also supporting a surface upon which ink or paint markings can be applied. One of ordinary skill will appreciate that the belt 12 need not circumnavigate, but could be spooled or stored at one end and fed through the wheels 16 to a destination location, without circumnavigation. This feature would be required if the operator desired a record of footprints longer than the circumnavigatory path of the paper through the wheels 16. Otherwise, the footprints 34 of the mouse 18 would overlap as the paper belt 36 continued to run.

The image collection device 28, in accordance with the present embodiment, is disposed beneath the paper belt 36. The image collection device 28 is in the form of a first pad 38A and a second pad 38B. The first pad 38A and second pad 38B can utilize different technologies, such as being an ink pad, or paint pad.

The first pad 38A and second pad 38B capture the image of the mouse 18 ambulating along the moving paper belt 36 above. The mouse 18 is motivated to move as the paper belt 36 moves. As the mouse 18 ambulates, the weight of the mouse 18 on its feet or paws forces the paper belt 36 to make contact with the first pad 38A and the second pad 38B. As the paper belt 36 makes contact with the first pad 38A and the second pad 38B, ink or paint transfers from the first pad 38A and the second pad 38B to form the footprints 34 on the paper belt 36. There is an area of no contact 40 between the locations of the feet or paws forming the footprints 34 where the paper belt 36 does not make contact with the first pad 38A or the second pad 38B. This prevents errant marks from forming on the paper belt 36.

Once a desired amount of footprints 34 are collected on the paper belt 36, the paper belt 36 can be removed from the wheels 16 and analysis performed to determine locomotion kinematics of the mouse 18 based on the placement of the footprints 34. The first pad 38A, due to its more forward position, records the placement of the two front feet or paws, and the second pad 38B records the placement of the two back feet or paws. To differentiate the footprints 34, the first pad 38A can contain ink or paint of a first color (e.g. red), and the second pad 38B can contain ink or paint of a second color (e.g. blue). Thus the footprints 34 are more easily identified.

The first pad 38A and the second pad 38B can also take the form of a touch pad, or other pressure sensing pad or technology. In such an instance, the belt can be the paper belt 36 or the previously described belt 12, or even a belt with any variation of transparency, or no transparency. As the mouse ambulates, the feet or paws apply pressure at the footprints 34 to the first pad 38A and the second pad 38B. This pressure translates to an electronic signal received by the computing apparatus 30. The computing apparatus 30 manipulates the electronic signal to depict the footprints 34 for analysis.

Figure 6:
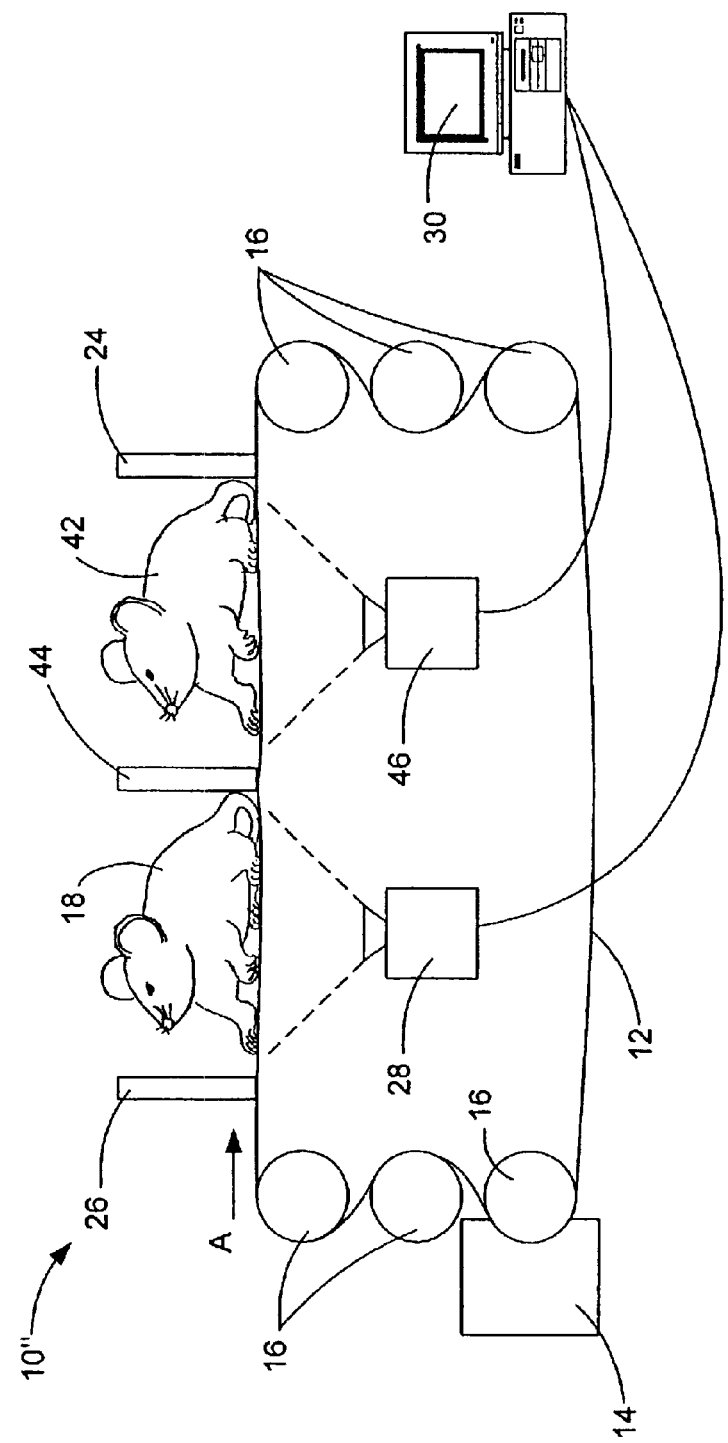
FIG. 6 is a diagrammatic illustration of still another embodiment of the locomotion monitoring apparatus, according to one aspect of the present invention.

FIG. 6 illustrates still another example embodiment in accordance with the teachings of the present invention. A locomotion monitoring apparatus 10" is shown. As with previous embodiments, the belt 12 passes through the plurality of wheels 16, and can be powered by the motor 14. The present embodiment includes the image collection device 28 and an additional second image collection device 46. In addition to the back partition 24 and front partition 26, a middle partition 44 creates two areas for mice to occupy. Therefore, the first mouse 18 can be ambulating along the moving belt 12 while a second mouse 42 is also ambulating along the same belt 12 contemporaneously. One of ordinary skill in the art will appreciate that there can be a plurality of middle partitions between the front partition 26 and back partition 24 to create a plurality of areas in which mice can ambulate on the moving belt. The illustrated embodiment is merely an example showing how such partitioning can be executed.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

What is claimed is:

1. A gait imaging system, comprising:
   a movable belt track upon which a subject can ambulate, the belt track having a transparency that obscures portions of the subject not contacting the belt track relative to portions of the subject contacting the belt track;
   an imaging device disposed below the belt track to record contact between the belt track and the portions of the subject contacting the belt track, wherein the portions of the subject contacting the belt track are recordable by the imaging device, thus enabling the identification of the placement position of at least one limb of the subject that makes contact with the belt track; and;
   wherein the subject can ambulate along the belt track in a substantially stationary location above the imaging device as the belt track moves, and the imaging device can record the contact by the subject, and wherein no physical contact is required between the belt track and the imaging device.

2. The system of claim 1, wherein the imaging device comprises a camera.

3. The system of claim 1, wherein the imaging device comprises at least one of a camcorder and a digital image capturing device, suitable for recording ambulation of the subject over a desired period of time.

4. The system of claim 1, wherein the speed of movement of the belt track is adjustable.

5. The system of claim 1, further comprising a structure disposed to substantially surround the subject while the subject is on the belt track, for motivating the subject to ambulate when the belt track is moving and prevent the subject from escape.

6. The system of claim 5, wherein the structure comprises a plurality of walls forming an enclosure hovering above the moving belt track.

7. The system of claim 6, wherein the structure further comprises one or more additional enclosures for motivating more than one subject to ambulate concomitantly.

8. The system of claim 1, further comprising a computing apparatus supporting a software application for manipulating and analyzing the data from the recorded subject contact.

9. The system of claim 8, wherein the software application identifies placement of the at least one limb of the subject based on the recorded subject contact.

10. The system of claim 8, wherein the software application executes at least one algorithm for analysis of a gait of the subject based at least in part on the subject contact.

11. The system of claim 1, wherein the imaging device can record images at a rate of at least about 60 frames per second.

12. A method of recording a gait of an ambulating subject, comprising:
    locating the subject on a movable belt track, the belt track having a transparency that obscures portions of the subject not contacting the belt track relative to portions of the subject contacting the belt track;
    motivating the subject to ambulate along the movable belt track at about the same rate as the movable belt track, while the belt track is moving, such that the location of the subject does not substantially change; and
    recording contact with the belt track made by a portion of at least one limb of the subject that makes contact with the belt track using a recording device underneath the belt track to identify placement position of the portion of the at least one limb of the subject that makes contact with the belt track based on the contact with the belt track;
    wherein the recording device can record the contact without making physical contact with the belt track.

13. The method according to claim 12, wherein locating comprises placing the subject within an enclosure hovering above the movable belt track.

14. The method according to claim 12, wherein motivating the subject comprises initiating movement of the belt track while the subject is surrounded by an enclosure, such that the subject must ambulate to avoid collision with the enclosure.

15. The method according to claim 12, wherein recording comprises utilizing at least one of a camcorder and a digital image capturing device to record contact made by the at least one limb of the subject with the belt track for a desired period of time.

16. The method according to claim 12, wherein the belt track is sufficiently transparent to enable viewing of the contact made by the at least one limb from underneath the belt track.

17. The method according to claim 12, further comprising forwarding information relating to the contact made by the at least one limb to a computing apparatus supporting a software application for analyzing the gait of the subject based on the recorded contact.

18. The method according to claim 17, further comprising reading the information to a data storage device.

19. The method according to claim 17, further comprising converting the information to a standardized format.

20. The method according to claim 12, wherein recording occurs at a rate of at least about 60 frames per second.

21. The method according to claim 12, further comprising identifying footprint image data from the contact made by at least one limb of the subject with the belt track.

22. The method according to claim 21, wherein identifying footprint image data comprises converting image data to binary and filtering out noise.

23. The method according to claim 21, further comprising calculating physiological information based on the footprint image data.

24. A gait imaging system, comprising:
    a movable belt track upon which a subject can ambulate;
    an imaging device disposed below the belt track to record contact between at least one limb of the subject and the belt track;
    wherein the subject can ambulate along the belt track in a substantially stationary location above the imaging device as the belt track moves, and the imaging device can record the contact by the subject; and
    wherein the imaging device comprises a reservoir of ink upon which the at least one limb of the subject can apply pressure, through the belt track, transferring ink from the reservoir to the markable surface of the belt track.

25. A method of recording a gait of an ambulating subject, comprising:
    locating the subject on a movable belt track;
    motivating the subject to ambulate along the movable belt track at about the same rate as the movable belt track, while the belt track is moving, such that the location of the subject does not substantially change; and
    recording contact made by at least one limb of the subject with the belt track with a recording device underneath the belt track;
    wherein recording comprises transferring ink from an ink reservoir underneath the belt track to a markable surface of the belt track upon each instance of the at least one limb of the subject applying pressure, through the belt track, to the ink reservoir.

* * * * *